United States Patent
Arruda et al.

(10) Patent No.: US 12,252,528 B2
(45) Date of Patent: Mar. 18, 2025

(54) COMPOSITIONS AND METHODS FOR MODULATING FACTOR VIII FUNCTION

(71) Applicant: THE CHILDREN'S HOSPITAL OF PHILADELPHIA, Philadelphia, PA (US)

(72) Inventors: Valder R. Arruda, Philadelphia, PA (US); Benjamin Samelson-Jones, Wynnewood, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 529 days.

(21) Appl. No.: 17/279,961

(22) PCT Filed: Oct. 23, 2019

(86) PCT No.: PCT/US2019/057609
§ 371 (c)(1),
(2) Date: Mar. 25, 2021

(87) PCT Pub. No.: WO2020/086686
PCT Pub. Date: Apr. 30, 2020

(65) Prior Publication Data
US 2022/0033475 A1    Feb. 3, 2022

Related U.S. Application Data

(60) Provisional application No. 62/749,182, filed on Oct. 23, 2018.

(51) Int. Cl.
*C07K 14/755*    (2006.01)
*A61K 38/00*    (2006.01)

(52) U.S. Cl.
CPC ............ *C07K 14/755* (2013.01); *A61K 38/00* (2013.01)

(58) Field of Classification Search
CPC ... A61K 38/00; A61P 7/04; A61P 7/08; C07K 14/755
See application file for complete search history.

(56) References Cited

U.S. PATENT DOCUMENTS 6,358,703 B1 *  3/2002  Cho ................... A61P 7/00
                                                 435/69.6
7,459,534 B2 * 12/2008  Kaufman ........... C07K 14/755
                                                  530/381

(Continued)

FOREIGN PATENT DOCUMENTS

WO          94/11503 A2    5/1994
WO    WO-9703195 A1 *      1/1997  ........... C07K 14/755

(Continued)

OTHER PUBLICATIONS

GenBank: ABV90867.1, B domain-deleted coagulation factor VIII [synthetic construct], NCBI Protein Database, 2 pages (Jul. 23, 2009), also available at https://www.ncbi.nlm.nih.gov/protein/ABV90867.1 (last visited Oct. 17, 2023) (Year: 2009).*

(Continued)

*Primary Examiner* — Randall L Beane
(74) *Attorney, Agent, or Firm* — Robert C. Netter, Jr.; Dann, Dorfman, Herrell & Skillman

(57) ABSTRACT

Factor VIII variants and methods of use thereof are disclosed.

27 Claims, 5 Drawing Sheets
Specification includes a Sequence Listing.

(56) References Cited

U.S. PATENT DOCUMENTS

| | | | |
|---|---|---|---|
| 8,816,054 B2 | 8/2014 | Arruda et al. | |
| 9,670,267 B2 | 6/2017 | Arruda et al. | |
| 2003/0148953 A1 | 8/2003 | Kaufman et al. | |
| 2004/0137579 A1 | 7/2004 | Chapman et al. | |
| 2004/0248785 A1 | 12/2004 | Saenko et al. | |
| 2008/0300174 A1 | 12/2008 | Xiao | |
| 2014/0057848 A1 | 2/2014 | Meems et al. | |
| 2014/0308280 A1* | 10/2014 | Maloney | C07K 14/755 514/14.1 |
| 2015/0158929 A1 | 6/2015 | Schellenberger et al. | |
| 2015/0224203 A1 | 8/2015 | Behrens et al. | |
| 2019/0330311 A1* | 10/2019 | Oh | A61P 7/04 |

FOREIGN PATENT DOCUMENTS

| | | | |
|---|---|---|---|
| WO | 01/70968 A3 | 9/2001 | |
| WO | 2005/047322 A2 | 5/2005 | |
| WO | WO-2006027111 A1 * | 3/2006 | C07K 14/755 |
| WO | 2009/058446 A1 | 5/2009 | |
| WO | 2009/089396 A2 | 7/2009 | |
| WO | 2012/035050 A2 | 3/2012 | |
| WO | 2012/170289 A1 | 12/2012 | |
| WO | 2013/160005 A1 | 10/2013 | |
| WO | 2014/026954 A1 | 2/2014 | |
| WO | WO-2015106052 A1 * | 7/2015 | A61K 38/37 |
| WO | WO-2017222337 A1 * | 12/2017 | A61P 7/00 |

OTHER PUBLICATIONS

Griffiths et al., Factor VIIIa A2 subunit shows a high affinity interaction with factor IXa: contribution of A2 subunit residues 707-714 to the interaction with factor IXa. J Biol Chem., May 24, 2013; vol. 288(21):15057-64 (Epub Apr. 11, 2013) (Year: 2013).*

Graur, D. (2006). Single-base Mutation, In Encyclopedia of Life Sciences, (Ed.)., 4 pages, John Wiley & Sons, Ltd, https://doi.org/10.1038/npg.els.0005093 (Year: 2006).*

Lind et al., Novel forms of B-domain-deleted recombinant factor VIII molecules Construction and biochemical characterization, Eur. J. Biochem., vol. 232:19-27 (1995) (Year: 1995).*

Lind, et al., "Novel forms of B-domain-deleted recombinant factor VIII molecules. Construction and biochemical 2 characterization" Eur. J. Biochem. (1995) 232(1):19-27.

Siner, et al.,"Circumventing furin enhances factor VIII biological activity and ameliorates bleeding phenotypes in hemophilia models" JCI Insight (2016) 1(16):e89371.

Pittman, et al., "Biochemical, immunological, and in vivo functional characterization of B-domain-deleted factor VIII" Blood (1993) 81(11):2925-35.

Toole, et al., "A large region (approximately equal to 95 kDa) of human factor VIII is dispensable for in vitro procoagulant activity" Proc. Natl. Acad. Sci. (1986) 83(16):5939-42.

Samelson-Jones, et al., "Protein-Engineered Coagulation Factors for Hemophilia Gene Therapy" Molecular Therapy: Methods & Clinical Development (Dec. 31, 2018) 12:184-201.

* cited by examiner

```
A TRRYYLGAVE LSWDYMQSDL GELPVDARFP PRVPKSFPFN
TSVVYKKTLF VEFTDHLFNI AKPRPPWMGL LGPTIQAEVY DTVVITLKNM ASHPVSLHAV
GVSYWKASEG AEYDDQTSQR EKEDDKVFPG GSHTYVWQVL KENGPMASDP LCLTYSYLSH
VDLVKDLNSG LIGALLVCRE GSLAKEKTQT LHKFILLFAV FDEGKSWHSE TKNSLMQDRD
AASARAWPKM HTVNGYVNRS LPGLIGCHRK SVYWHVIGMG TTPEVHSIFL EGHTFLVRNH
RQASLEISPI TFLTAQTLLM DLGQFLLFCH ISSHQHDGME AYVKVDSCPE EPQLRMKNNE
EAEDYDDDLT DSEMDVVRFD DDNSPSFIQI RSVAKKHPKT WVHYIAAEEE DWDYAPLVLA
PDDRSYKSQY LNNGPQRIGR KYKKVRFMAY TDETFKTREA IQHESGILGP LLYGEVGDTL
LIIFKNQASR PYNIYPHGIT DVRPLYSRRL PKGVKHLKDF PILPGEIFKY KWTVTVEDGP
TKSDPRCLTR YYSSFVNMER DLASGLIGPL LICYKESVDQ RGNQIMSDKR NVILFSVFDE
NRSWYLTENI QRFLPNPAGV QLEDPEFQAS NIMHSINGYV FDSLQLSVCL HEVAYWYILS
IGAQTDFLSV FFSGYTFKHK MVYEDTLTLF PFSGETVFMS MENPGLWILG CHNSDFRNRG
MTALLKVSSC DKNTGDYYED SYEDISAYLL SKNNAIEPR*S* *FSQNSRHPST* *RQKQFNATTI*
*PENDIEKTDP* *WFAHRTPMPK* *IQNVSSSDLL* *MLLRQSPTPH* *GLSLSDLQEA* *KYETFSDDPS*
*PGAIDSNNSL* *SEMTHFRPQL* *HHSGDMVFTP* *ESGLQLRLNE* *KLGTTAATEL* *KKLDFKVSST*
*SNNLISTIPS* *DNLAAGTDNT* *SSLGPPSMPV* *HYDSQLDTTL* *FGKKSSPLTE* *SGGPLSLSEE*
*NNDSKLLESG* *LMNSQESSWG* *KNVSSTESGR* *LFKGKRAHGP* *ALLTKDNALF* *KVSISLLKTN*
*KTSNNSATNR* *KTHIDGPSLL* *IENSPSVWQN* *ILESDTEFKK* *VTPLIHDRML* *MDKNATALRL*
*NHMSNKTTSS* *KNMEMVQQKK* *EGPIPPDAQN* *PDMSFFKMLF* *LPESARWIQR* *THGKNSLNSG*
*QGPSPKQLVS* *LGPEKSVEGQ* *NFLSEKNKVV* *VGKGEFTKDV* *GLKEMVFPSS* *RNLFLTNLDN*
*LHENNTHNQE* *KKIQEEIEKK* *ETLIQENVVL* *PQIHTVTGTK* *NFMKNLFLLS* *TRQNVEGSYD*
*GAYAPVLQDF* *RSLNDSTNRT* *KKHTAHFSKK* *GEEENLEGLG* *NQTKQIVEKY* *ACTTRISPNT*
*SQQNFVTQRS* *KRALKQFRLP* *LEETELEKRI* *IVDDTSTQWS* *KNMKHLTPST* *LTQIDYNEKE*
*KGAITQSPLS* *DCLTRSHSIP* *QANRSPLPIA* *KVSSFPSIRP* *IYLTRVLFQD* *NSSHLPAASY*
*RKKDSGVQES* *SHFLQGAKKN* *NLSLAILTLE* *MTGDQREVGS* *LGTSATNSVT* *YKKVENTVLP*
*KPDLPKTSGK* *VELLPKVHIY* *QKDLFPTETS* *NGSPGHLDLV* *EGSLLQGTEG* *AIKWNEANRP*
*GKVPFLRVAT* *ESSAKTPSKL* *LDPLAWDNHY* *GTQIPKEEWK* *SQEKSPEKTA* *FKKKDTILSL*
*NACESNHAIA* *AINEGQNKPE* *IEVTWAKQGR* *TERLCSQNPP* *VLKRHQR*EIT RTTLQSDQEE
IDYDDTISVE MKKEDFDIYD EDENQSPRSF QKKTRHYFIA AVERLWDYGM SSSPHVLRNR
AQSGSVPQFK KVVFQEFTDG SFTQPLYRGE LNEHLGLLGP YIRAEVEDNI MVTFRNQASR
PYSFYSSLIS YEEDQRQGAE PRKNFVKPNE TKTYFWKVQH HMAPTKDEFD CKAWAYFSDV
DLEKDVHSGL IGPLLVCHTN TLNPAHGRQV TVQEFALFFT IFDETKSWYF TENMERNCRA
PCNIQMEDPT FKENYRFHAI NGYIMDTLPG LVMAQDQRIR WYLLSMGSNE NIHSIHFSGH
VFTVRKKEEY KMALYNLYPG VFETVEMLPS KAGIWRVECL IGEHLHAGMS TLFLVYSNKC
QTPLGMASGH IRDFQITASG QYGQWAPKLA RLHYSGSINA WSTKEPFSWI KVDLLAPMII
HGIKTQGARQ KFSSLYISQF IIMYSLDGKK WQTYRGNSTG TLMVFFGNVD SSGIKHNIFN
PPIIARYIRL HPTHYSIRST LRMELMGCDL NSCSMPLGME SKAISDAQIT ASSYFTNMFA
TWSPSKARLH LQGRSNAWRP QVNNPKEWLQ VDFQKTMKVT GVTTQGVKSL LTSMYVKEFL
ISSSQDGHQW TLFFQNGKVK VFQGNQDSFT PVVNSLDPPL LTRYLRIHPQ SWVHQIALRM
EVLGCEAQDL Y
```

Figure 4

SEQUENCE LISTING

<160> NUMBER OF SEQ ID NOS: 18

<210> SEQ ID NO 1
<211> LENGTH: 2332
<212> TYPE: PRT
<213> ORGANISM: Homo sapiens

<400> SEQUENCE: 1

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365
```

-continued

```
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                    405                 410                 415
Gln Arg Ile Gly Arg Lys Tyr Lys Val Arg Phe Met Ala Tyr Thr
                420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
                515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
                595                 600                 605
Gln Ala Ser Asn Ile Met His Ser Ile Asn Gly Tyr Val Phe Asp Ser
                610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
                675                 680                 685
Ile Leu Gly Cys His Asn Ser Asp Phe Arg Asn Arg Gly Met Thr Ala
690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
                740                 745                 750
Gln Lys Gln Phe Asn Ala Thr Thr Ile Pro Glu Asn Asp Ile Glu Lys
                755                 760                 765
Thr Asp Pro Trp Phe Ala His Arg Thr Pro Met Pro Lys Ile Gln Asn
770                 775                 780
Val Ser Ser Ser Asp Leu Leu Met Leu Leu Arg Gln Ser Pro Thr Pro
```

-continued

```
            785                 790                 795                 800
His Gly Leu Ser Leu Ser Asp Leu Gln Glu Ala Lys Tyr Glu Thr Phe
                    805                 810                 815

Ser Asp Asp Pro Ser Pro Gly Ala Ile Asp Ser Asn Asn Ser Leu Ser
                    820                 825                 830

Glu Met Thr His Phe Arg Pro Gln Leu His His Ser Gly Asp Met Val
                    835                 840                 845

Phe Thr Pro Glu Ser Gly Leu Gln Leu Arg Leu Asn Glu Lys Leu Gly
        850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                    885                 890                 895

Gly Thr Asp Asn Thr Ser Ser Leu Gly Pro Pro Ser Met Pro Val His
                    900                 905                 910

Tyr Asp Ser Gln Leu Asp Thr Thr Leu Phe Gly Lys Lys Ser Ser Pro
                    915                 920                 925

Leu Thr Glu Ser Gly Gly Pro Leu Ser Leu Ser Glu Glu Asn Asn Asp
        930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                    965                 970                 975

Arg Ala His Gly Pro Ala Leu Leu Thr Lys Asp Asn Ala Leu Phe Lys
                    980                 985                 990

Val Ser Ile Ser Leu Leu Lys Thr Asn Lys Thr Ser Asn Asn Ser Ala
                    995                 1000                1005

Thr Asn Arg Lys Thr His Ile Asp Gly Pro Ser Leu Leu Ile Glu Asn
        1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
                    1045                1050                1055

Thr Ala Leu Arg Leu Asn His Met Ser Asn Lys Thr Thr Ser Ser Lys
                    1060                1065                1070

Asn Met Glu Met Val Gln Gln Lys Lys Glu Gly Pro Ile Pro Pro Asp
                    1075                1080                1085

Ala Gln Asn Pro Asp Met Ser Phe Phe Lys Met Leu Phe Leu Pro Glu
        1090                1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
                    1125                1130                1135

Ser Val Glu Gly Gln Asn Phe Leu Ser Glu Lys Asn Lys Val Val Val
                    1140                1145                1150

Gly Lys Gly Glu Phe Thr Lys Asp Val Gly Leu Lys Glu Met Val Phe
                    1155                1160                1165

Pro Ser Ser Arg Asn Leu Phe Leu Thr Asn Leu Asp Asn Leu His Glu
        1170                1175                1180

Asn Asn Thr His Asn Gln Glu Lys Lys Ile Gln Glu Ile Glu Lys
1185                1190                1195                1200

Lys Glu Thr Leu Ile Gln Glu Asn Val Val Leu Pro Gln Ile His Thr
                    1205                1210                1215
```

-continued

Val Thr Gly Thr Lys Asn Phe Met Lys Asn Leu Phe Leu Leu Ser Thr
        1220                1225                1230

Arg Gln Asn Val Glu Gly Ser Tyr Asp Gly Ala Tyr Ala Pro Val Leu
        1235                1240                1245

Gln Asp Phe Arg Ser Leu Asn Asp Ser Thr Asn Arg Thr Lys Lys His
        1250                1255                1260

Thr Ala His Phe Ser Lys Lys Gly Glu Glu Asn Leu Glu Gly Leu
1265                1270                1275                1280

Gly Asn Gln Thr Lys Gln Ile Val Glu Lys Tyr Ala Cys Thr Thr Arg
        1285                1290                1295

Ile Ser Pro Asn Thr Ser Gln Gln Asn Phe Val Thr Gln Arg Ser Lys
        1300                1305                1310

Arg Ala Leu Lys Gln Phe Arg Leu Pro Leu Glu Glu Thr Glu Leu Glu
        1315                1320                1325

Lys Arg Ile Ile Val Asp Asp Thr Ser Thr Gln Trp Ser Lys Asn Met
        1330                1335                1340

Lys His Leu Thr Pro Ser Thr Leu Thr Gln Ile Asp Tyr Asn Glu Lys
1345                1350                1355                1360

Glu Lys Gly Ala Ile Thr Gln Ser Pro Leu Ser Asp Cys Leu Thr Arg
        1365                1370                1375

Ser His Ser Ile Pro Gln Ala Asn Arg Ser Pro Leu Pro Ile Ala Lys
        1380                1385                1390

Val Ser Ser Phe Pro Ser Ile Arg Pro Ile Tyr Leu Thr Arg Val Leu
        1395                1400                1405

Phe Gln Asp Asn Ser Ser His Leu Pro Ala Ala Ser Tyr Arg Lys Lys
        1410                1415                1420

Asp Ser Gly Val Gln Glu Ser Ser His Phe Leu Gln Gly Ala Lys Lys
1425                1430                1435                1440

Asn Asn Leu Ser Leu Ala Ile Leu Thr Leu Glu Met Thr Gly Asp Gln
        1445                1450                1455

Arg Glu Val Gly Ser Leu Gly Thr Ser Ala Thr Asn Ser Val Thr Tyr
        1460                1465                1470

Lys Lys Val Glu Asn Thr Val Leu Pro Lys Pro Asp Leu Pro Lys Thr
        1475                1480                1485

Ser Gly Lys Val Glu Leu Leu Pro Lys Val His Ile Tyr Gln Lys Asp
        1490                1495                1500

Leu Phe Pro Thr Glu Thr Ser Asn Gly Ser Pro Gly His Leu Asp Leu
1505                1510                1515                1520

Val Glu Gly Ser Leu Leu Gln Gly Thr Glu Gly Ala Ile Lys Trp Asn
        1525                1530                1535

Glu Ala Asn Arg Pro Gly Lys Val Pro Phe Leu Arg Val Ala Thr Glu
        1540                1545                1550

Ser Ser Ala Lys Thr Pro Ser Lys Leu Leu Asp Pro Leu Ala Trp Asp
        1555                1560                1565

Asn His Tyr Gly Thr Gln Ile Pro Lys Glu Glu Trp Lys Ser Gln Glu
        1570                1575                1580

Lys Ser Pro Glu Lys Thr Ala Phe Lys Lys Asp Thr Ile Leu Ser
1585                1590                1595                1600

Leu Asn Ala Cys Glu Ser Asn His Ala Ile Ala Ala Ile Asn Glu Gly
        1605                1610                1615

Gln Asn Lys Pro Glu Ile Glu Val Thr Trp Ala Lys Gln Gly Arg Thr
        1620                1625                1630

```
Glu Arg Leu Cys Ser Gln Asn Pro Val Leu Lys Arg His Gln Arg
        1635                1640                1645

Glu Ile Thr Arg Thr Thr Leu Gln Ser Asp Gln Glu Ile Asp Tyr
        1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
                1685                1690                1695

His Tyr Phe Ile Ala Ala Val Glu Arg Leu Trp Asp Tyr Gly Met Ser
            1700                1705                1710

Ser Ser Pro His Val Leu Arg Asn Arg Ala Gln Ser Gly Ser Val Pro
        1715                1720                1725

Gln Phe Lys Lys Val Val Phe Gln Glu Phe Thr Asp Gly Ser Phe Thr
        1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
            1765                1770                1775

Asn Gln Ala Ser Arg Pro Tyr Ser Phe Tyr Ser Ser Leu Ile Ser Tyr
        1780                1785                1790

Glu Glu Asp Gln Arg Gln Gly Ala Glu Pro Arg Lys Asn Phe Val Lys
        1795                1800                1805

Pro Asn Glu Thr Lys Thr Tyr Phe Trp Lys Val Gln His His Met Ala
        1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
            1845                1850                1855

Val Cys His Thr Asn Thr Leu Asn Pro Ala His Gly Arg Gln Val Thr
        1860                1865                1870

Val Gln Glu Phe Ala Leu Phe Phe Thr Ile Phe Asp Glu Thr Lys Ser
        1875                1880                1885

Trp Tyr Phe Thr Glu Asn Met Glu Arg Asn Cys Arg Ala Pro Cys Asn
        1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
            1925                1930                1935

Asp Gln Arg Ile Arg Trp Tyr Leu Leu Ser Met Gly Ser Asn Glu Asn
        1940                1945                1950

Ile His Ser Ile His Phe Ser Gly His Val Phe Thr Val Arg Lys Lys
        1955                1960                1965

Glu Glu Tyr Lys Met Ala Leu Tyr Asn Leu Tyr Pro Gly Val Phe Glu
        1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
            2005                2010                2015

Tyr Ser Asn Lys Cys Gln Thr Pro Leu Gly Met Ala Ser Gly His Ile
        2020                2025                2030

Arg Asp Phe Gln Ile Thr Ala Ser Gly Gln Tyr Gly Gln Trp Ala Pro
        2035                2040                2045

Lys Leu Ala Arg Leu His Tyr Ser Gly Ser Ile Asn Ala Trp Ser Thr
```

```
              2050                2055                2060
Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
                2085                2090                2095

Tyr Ile Ser Gln Phe Ile Ile Met Tyr Ser Leu Asp Gly Lys Lys Trp
                2100                2105                2110

Gln Thr Tyr Arg Gly Asn Ser Thr Gly Thr Leu Met Val Phe Phe Gly
            2115                2120                2125

Asn Val Asp Ser Ser Gly Ile Lys His Asn Ile Phe Asn Pro Pro Ile
2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
                2165                2170                2175

Pro Leu Gly Met Glu Ser Lys Ala Ile Ser Asp Ala Gln Ile Thr Ala
                2180                2185                2190

Ser Ser Tyr Phe Thr Asn Met Phe Ala Thr Trp Ser Pro Ser Lys Ala
                2195                2200                2205

Arg Leu His Leu Gln Gly Arg Ser Asn Ala Trp Arg Pro Gln Val Asn
            2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
                2245                2250                2255

Val Lys Glu Phe Leu Ile Ser Ser Ser Gln Asp Gly His Gln Trp Thr
                2260                2265                2270

Leu Phe Phe Gln Asn Gly Lys Val Lys Val Phe Gln Gly Asn Gln Asp
            2275                2280                2285

Ser Phe Thr Pro Val Val Asn Ser Leu Asp Pro Pro Leu Leu Thr Arg
            2290                2295                2300

Tyr Leu Arg Ile His Pro Gln Ser Trp Val His Gln Ile Ala Leu Arg
2305                2310                2315                2320

Met Glu Val Leu Gly Cys Glu Ala Gln Asp Leu Tyr
                2325                2330

<210> SEQ ID NO 2
<211> LENGTH: 19
<212> TYPE: PRT
<213> ORGANISM: Homo sapiens

<400> SEQUENCE: 2

Met Gln Ile Glu Leu Ser Thr Cys Phe Phe Leu Cys Leu Leu Arg Phe
1               5                   10                  15

Cys Phe Ser

<210> SEQ ID NO 3
<211> LENGTH: 14
<212> TYPE: PRT
<213> ORGANISM: Artificial Sequence
<220> FEATURE:
<223> OTHER INFORMATION: peptide linker

<400> SEQUENCE: 3

Ser Phe Ser Gln Asn Pro Pro Val Leu Lys Arg His Gln Arg
1               5                   10
```

```
<210> SEQ ID NO 4
<211> LENGTH: 21
<212> TYPE: PRT
<213> ORGANISM: Artificial Sequence
<220> FEATURE:
<223> OTHER INFORMATION: peptide linker

<400> SEQUENCE: 4

Ser Phe Ser Gln Asn Ser Arg His Pro Ser Gln Asn Pro Pro Val Leu
1               5                   10                  15

Lys Arg His Gln Arg
            20

<210> SEQ ID NO 5
<211> LENGTH: 24
<212> TYPE: PRT
<213> ORGANISM: Artificial Sequence
<220> FEATURE:
<223> OTHER INFORMATION: peptide linker

<400> SEQUENCE: 5

Ser Phe Ala Gln Asn Ser Arg Pro Pro Ser Ala Ser Ala Pro Lys Pro
1               5                   10                  15

Pro Val Leu Arg Arg His Gln Arg
            20

<210> SEQ ID NO 6
<211> LENGTH: 16
<212> TYPE: PRT
<213> ORGANISM: Artificial Sequence
<220> FEATURE:
<223> OTHER INFORMATION: peptide linker

<400> SEQUENCE: 6

Ser Phe Ser Gln Asn Ser Arg His Gln Ala Tyr Arg Tyr Arg Arg Gly
1               5                   10                  15

<210> SEQ ID NO 7
<211> LENGTH: 31
<212> TYPE: PRT
<213> ORGANISM: Artificial Sequence
<220> FEATURE:
<223> OTHER INFORMATION: peptide linker

<400> SEQUENCE: 7

Ser Phe Ser Gln Asn Ala Thr Asn Val Ser Asn Asn Ser Asn Thr Ser
1               5                   10                  15

Asn Asp Ser Asn Val Ser Pro Pro Val Leu Lys Arg His Gln Arg
            20                  25                  30

<210> SEQ ID NO 8
<211> LENGTH: 14
<212> TYPE: PRT
<213> ORGANISM: Artificial Sequence
<220> FEATURE:
<223> OTHER INFORMATION: peptide linker

<400> SEQUENCE: 8

Ser Phe Ser Gln Asn Pro Pro Val Leu Lys His His Gly Arg
1               5                   10

<210> SEQ ID NO 9
<211> LENGTH: 10
<212> TYPE: PRT
<213> ORGANISM: Artificial Sequence
```

```
<220> FEATURE:
<223> OTHER INFORMATION: peptide linker

<400> SEQUENCE: 9

Ser Phe Ser Gln Asn Pro Pro Val Leu Lys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: peptide linker

<400> SEQUENCE: 10

Ser Phe Ser Gln Asn Pro Pro Val Ser Lys His His Gln Arg
1               5                   10

<210> SEQ ID NO 11
<211> LENGTH: 14
<212> TYPE: PRT
<213> ORGANISM: Artificial Sequence
<220> FEATURE:
<223> OTHER INFORMATION: peptide linker

<400> SEQUENCE: 11

Ser Phe Ser Gln Asn Pro Pro Val Ser Lys Arg His Gln Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: peptide linker

<400> SEQUENCE: 12

Ser Phe Ser Gln Asn Pro Pro Val Ser Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: peptide linker

<400> SEQUENCE: 13

Ser Phe Ser Gln Asn Ser Arg His Pro Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: peptide linker

<400> SEQUENCE: 14

Ser Phe Ser Gln Asn Ser Arg His Pro Ser Thr Arg Gln Lys Gln
1               5                   10                  15

<210> SEQ ID NO 15
<211> LENGTH: 20
<212> TYPE: PRT
<213> ORGANISM: Artificial Sequence
<220> FEATURE:
```

```
<223> OTHER INFORMATION: peptide linker

<400> SEQUENCE: 15

Ser Phe Ser Gln Asn Ser Arg His Pro Ser Thr Arg Gln Lys Gln Phe
1               5                   10                  15

Asn Ala Thr Thr
            20

<210> SEQ ID NO 16
<211> LENGTH: 5
<212> TYPE: PRT
<213> ORGANISM: Artificial Sequence
<220> FEATURE:
<223> OTHER INFORMATION: peptide linker

<400> SEQUENCE: 16

Ser Phe Ser Gln Asn
1               5

<210> SEQ ID NO 17
<211> LENGTH: 8
<212> TYPE: PRT
<213> ORGANISM: Artificial Sequence
<220> FEATURE:
<223> OTHER INFORMATION: peptide linker

<400> SEQUENCE: 17

Ser Phe Ser Gln Asn Ser Arg His
1               5

<210> SEQ ID NO 18
<211> LENGTH: 30
<212> TYPE: PRT
<213> ORGANISM: Artificial Sequence
<220> FEATURE:
<223> OTHER INFORMATION: peptide linker

<400> SEQUENCE: 18

Ser Phe Ser Gln Asn Ser Arg His Pro Ser Thr Arg Gln Lys Gln Phe
1               5                   10                  15

Asn Ala Thr Thr Ile Pro Glu Asn Asp Ile Glu Lys Thr Asp
            20                  25                  30
```

COMPOSITIONS AND METHODS FOR MODULATING FACTOR VIII FUNCTION

This application is a § 371 application of PCT/US2019/057609, filed Oct. 23, 2019, which claims priority under 35 U.S.C. § 119 (e) to U.S. Provisional Patent Application No. 62/749,182, filed Oct. 23, 2018. The foregoing applications are is incorporated by reference herein.

This invention was made with government support under Grant Numbers R01 HL-137335-01A1 awarded by the National Institutes of Health. The government has certain rights in the invention.

FIELD OF THE INVENTION

The present invention relates to the fields of medicine and hematology. More specifically, the invention provides novel Factor VIII variants and methods of using the same to modulate the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

Mutations in Factor VIII (FVIII) can lead to severe bleeding disorders and are associated with hemophilia A. Defective FVIII or a lack of FVIII activity results in an inability to effectively form clots. To date, only 20% of patients with hemophilia A worldwide receive regular treatment with FVIII replacement therapy due its high cost. Typically, the FVIII is plasma-derived or recombinantly produced. Gene therapy for hemophilia A based on AAV vectors is promising, but there is a safety limitation due to aberrant immune responses to the vector. This aberrant immune response has been found to be vector-dose dependent. Moreover, regardless of the use of administered protein or gene therapy, the immunogenicity of the delivered or expressed FVIII can be problematic. Indeed, 20-30% of hemophilia A patients develop inhibitors (e.g., anti-FVIII neutralizing antibodies) to the treatment (Peyvandi, et al., N. Engl. J. Med. (2016) 374:2054-2064; Walsh, et al., Am. J. Hematol. (2015) 90:400-405; Eckhardt, et al., J. Thromb. Haemost. (2015) 13:1217-1225; Darby, et al., J. Thromb. Haemost. (2004) 2:1047-1054; Donfield, et al., Blood (2007) 110:3656-3661; Witmer, et al., Br. J. Haematol. (2011) 152:211-216; Hoots, W. K., Semin. Hematol. (2008) 45(2 Suppl 1):S42-S49; Guh, et al., Haemophilia (2012) 18:268-275; Lindvall, et al., Pediatr. Blood Cancer (2014) 61:706-711). Thus, generating enhanced FVIII molecules would benefit the treatment of hemophilia by lowering the cost of FVIII production, increasing the safety of AAV gene therapy, and/or reducing immunogenicity. Therefore, there is an obvious need for FVIII molecules with improved biological properties.

SUMMARY OF THE INVENTION

In accordance with the present invention, compositions and methods for the modulation of hemostasis in patients in need thereof are provided. More specifically, Factor VIII (FVIII) variants which modulate (e.g., increase) hemostasis are provided. In a particular embodiment, the B-domain of the FVIII variant is replaced with an amino acid sequence having at least 90% identity with SEQ ID NO: 13, SEQ ID NO: 14, SEQ ID NO: 15, SEQ ID NO: 16, SEQ ID NO: 17, or SEQ ID NO: 18. In a particular embodiment, the B-domain of the FVIII variant is replaced with an amino acid sequence comprising SEQ ID NO: 18. In a particular embodiment, the Factor VIII variant comprises at least one mutation at position 560, 561, 712, 713, and/or 659, optionally with the B-domain replacement. In a particular embodiment, the FVIII variant comprises a substitution of the Lys at position 659 with another amino acid. In a particular embodiment, the Lys at position 659 is substituted with Trp, Arg, Ala, His, Tyr, Asp, Thr, Ser, Val, Phe, Gln, or Cys, particularly Ser, Gln, or Cys. The FVIII variants may comprise the B-domain substitution and the substitution at position 659. Compositions comprising at least one FVIII variant of the instant invention and at least one pharmaceutically acceptable carrier are also provided. Nucleic acid molecules encoding the FVIII variants of the invention are also disclosed as are methods of use thereof. Another aspect of the invention includes host cells expressing the FVIII variants described herein. Methods for isolating and purifying the FVIII variants are also disclosed.

Pharmaceutical compositions comprising the FVIII variants and/or FVIII variant encoding nucleic acid molecules of the invention in a carrier are also provided. The invention also includes methods for the treatment of a hemostasis related disorder in a patient in need thereof comprising administration of a therapeutically effective amount of the FVIII variant and/or FVIII variant encoding nucleic acid molecules, particularly within a pharmaceutical composition. Such methods have efficacy in the treatment of disorders where a pro-coagulant is needed and include, without limitation, hemophilia, particularly hemophilia A.

BRIEF DESCRIPTION OF THE DRAWINGS

FIG. 4 provides an amino acid sequence of FVIII (SEQ ID NO: 1). The amino acids at positions 560, 561, 659, 712, and/or 713 are bolded and underlined. The B domain is also indicated with italics and bolding. The provided amino acid sequence lacks the 19 amino acid signal peptide at the N-terminus (MQIELSTCFFLCLLRFCFS (SEQ ID NO: 2)).

DETAILED DESCRIPTION OF THE INVENTION

Hemophilia A (HA) and hemophilia B (HB) are X-linked bleeding disorders due to inheritable deficiencies in either coagulation factor VIII (FVIII) or factor IX (FIX), respectively (Peyvandi, et al., Lancet (2016) 388:187-197; Konkle, et al., *Hemophilia A*. In GeneReviews, Adam, et al., eds., University of Washington (1993)). The bleeding phenotype is generally related to the residual factor activity: people with severe disease (factor activity <1% normal) have frequent spontaneous bleeds; people with moderate disease (factor activity 1%-5% normal) rarely have spontaneous bleeds, but bleed with minor trauma; and people with mild disease (factor activity 5%-40% normal) bleed during invasive procedures or trauma. Given this well-defined relationship between factor activity and bleeding phenotype, HA and HB are attractive targets for gene therapy as small increases in factor levels are expected to have a meaningful clinical impact. Although a variety of strategies have been investigated over several decades, the field has coalesced around the use of adeno-associated virus (AAV) vectors delivering transgenes of engineered FVIII or FIX variants with therapeutically advantageous properties not present in the wild-type (WT) protein (Hough, et al., J. Thromb. Haemost. (2005) 3:1195-1205; Lheriteau, et al., Blood Rev. (2015) 29:321-328; Rogers, et al., Front. Biosci. (2015) 20:556-603; Arruda, et al., Expert Opin. Orphan Drugs (2015) 3:997-1010; High, K. A., Hematology Am. Soc. Hematol. Educ. Program (2012) 2012:375-381; Zinn, et al., Curr. Opin. Virol. (2014) 8:90-97; Mingozzi, et al., Nat. Rev. Genet. (2011) 12:341-355; Colella, et al., Mol. Ther. Methods Clin. Dev. (2017) 8:87-104). Notably, full-length FVIII cDNA (7 kb) exceeds the packing capacity of AAV vectors (~4.7 kb). The removal of the B-domain of FVIII decreases the cDNA to ~4.4 kb. AAV-based clinical trials for HA have reported positive results using this approach (Rangarajan, et al., N. Engl. J. Med. (2017) 377:2519-2530).

As explained above, Factor VIII is central for coagulation activity and mutations in the FVIII gene result in hemophilia A, the most common form of hemophilia. Herein, specific changes in the amino acid sequence of FVIII are shown to be associated with enhanced protein production and activity. Thus, the instant invention provides rationally designed amino acid residue modifications which provide gain-of-function variants.

Figure 1A:
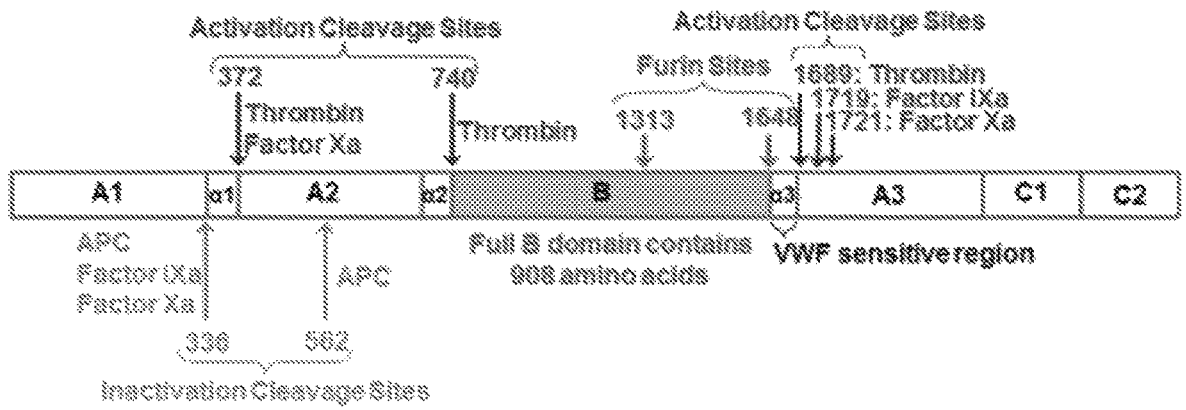
FIG. 1A provides a schematic of the Factor VIII protein. The full protein is 2332 amino acids in length and the B-domain is 908 amino acids. Various cleavage sites are also indicated in the schematic.
Figure 1B:
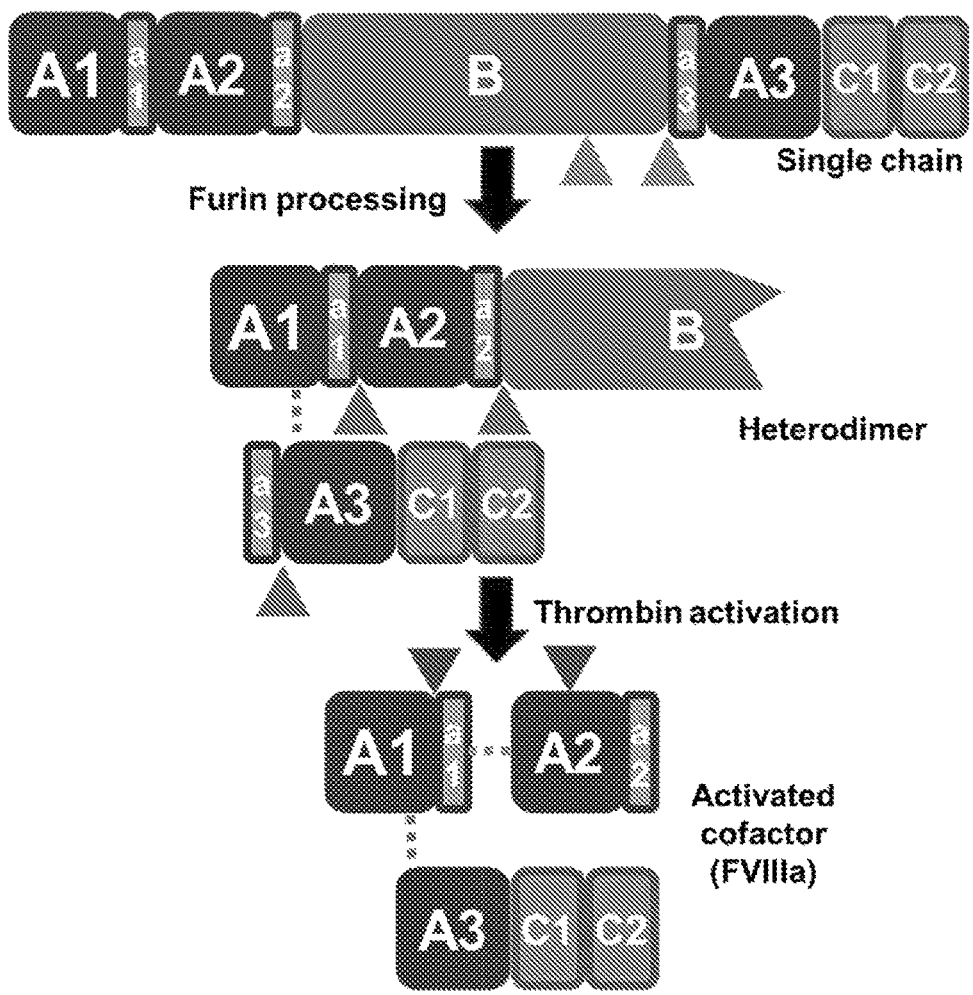
FIG. 1B provides a schematic of the processing of Factor VIII protein. FVIII is translated as a single-peptide chain (single chain) with the domain structure of A1-α1-A2-α2-B-α3-A3-C1-C2. Proteolytic cleavage of FVIII at R-1313 and/or R-1648 by the trans-Golgi protease furin (triangles) results in heterodimer formation. The FVIII heavy chain (A1-α1-A2-α2-B) and light chain (α3-A3-C1-C2) remain associated through non-covalent metal-ion-dependent interactions occurring between the A1 and A3 domains (dashes). The B-domain undergoes additional non-specific proteolysis in plasma after secretion. During coagulation, FVIII single chain or heterodimer is activated to its heterotrimeric cofactor form by cleavage by thrombin at R-372, R-740, and R-1689 (triangles). A2 remains associated with A1-α1 via non-covalent interactions (dashes). Inactivation of FVIIIa occurs via spontaneous A2 dissociation and/or proteolytic cleavage, primarily by activated protein C, at R-336 and R-562 (triangles).

Full-length FVIII is a large, 280-kDa protein primarily expressed in liver sinusoidal endothelial cells (LSECs), as well as extra-hepatic endothelial cells (Fahs, et al., Blood (2014) 123:3706-3713; Everett, et al., Blood (2014) 123: 3697-3705). FVIII predominantly circulates as a heterodimer of a heavy chain and a light chain bound through noncovalent metal-dependent interactions (Lenting, et al., Blood (1998) 92:3983-3996). Factor VIII comprises several domains. Generally, the domains are referred to as A1-A2-B-A3-C1-C2, as seen in FIG. 1. The heavy chain of FVIII comprises A1-A2-B and the light chain comprises A3-C1-C2. Initially, FVIII is in an inactive form bound to von Willebrand factor (vWF). FVIII is activated by cleavage by thrombin (Factor IIa) and release of the B domain. The activated form of FVIII (FVIIIa) separates from vWF and interacts with coagulation factor Factor IXa—leading to the formation of a blood clot via a coagulation cascade.

The B domain comprises 40% of the protein (908 amino acids) and is not required for the protein procoagulant activity (Brinkhous, et al., Proc. Natl. Acad. Sci. (1985) 82:8752-8756). The most common B-domain deleted (BDD) FVIII comprises 14 original amino acid residues as a linker (Lind, et al. (1995) Eur. J. Biochem., 232(1):19-27). This BDD FVIII is typically referred to as BDD-SQ or hFVIII-SQ (see Table 1). This BDD FVIII form is commonly used to produce recombinant BDD-FVIII (~4.4 Kb) as well for gene therapy (Berntorp, E., Semin. Hematol. (2001) 38(2 Suppl 4):1-3; Gouw, et al., N. Engl. J. Med. (2013) 368:231-239; Xi, et al., J. Thromb. Haemost. (2013) 11:1655-1662; Recht, et al., Haemophilia (2009) 15:869-880; Sabatino, et al., Mol. Ther. (2011) 19:442-449; Scallan, et al., Blood (2003) 102:2031-2037). As noted above, gene therapy using AAV vectors can only use shortened FVIII molecules such as a BDD-FVIII due to the limited packaging capacity of the AAV (4.7 Kb) and other vector systems (Lind, et al. (1995) Eur. J. Biochem., 232(1):19-27). U.S. Pat. No. 8,816,054 also provides BDD FVIII molecules with linkers of different lengths and sequences (see, e.g., Table 1). However, the linkers in Table 1 comprise more than one neo-epitope which can lead to the production of FVIII inhibitors.

TABLE 1

| Commercial Examples | Variant Name | Length (# aa) | (740)-Linker Sequence-(1649) |
|---|---|---|---|
| Xyntha, Eloctate | hFVIII-SQ* | 14 | SFSQNPPVLKRHQR |
| NovoEight, N8 GP | hFVIII-N8 | 21 | SFSQNSRHPSQNPPVLKRHQR |
| Obizur | pFVII-OL | 24 | SFAQNSRPPSASAPKPPVLRRHQR |
| Nuwiq | h-cl rhFVIII | 16 | SFSQNSRHQAYRYRRG |
| NA | hFVIII-V3 | 31 | SFSCINATNVSNNSNTSNDSNVSPPVLKRHQR |
| NA | hFVIII-RH | 14 | SFSQNPPVLKHHQR |
| NA | hFVIII-ΔF | 10 | SFSQNPPVLK |
| NA | cFVIII-SQ | 14 | SFSQNPPVSKHHQR |

TABLE 1-continued

| Commercial Examples | Variant Name | Length (# aa) | (740)-Linker Sequence-(1649) |
|---|---|---|---|
| NA | cFVIII-HR | 14 | SFSQNPPVSK<u>RHQR</u> |
| NA | cFVIII-ΔF | 10 | SFSQNPPVSK |

Short peptide linkers substituted for the B-domain in FVIII variants (Lind, et al. (1995) Eur. J. Biochem., 232(1):19-27; Pittman, et al., Blood (1993) 81:2925-2935; Toole, et al., Proc. Natl. Acad. Sci. (1986) 83:5939-5942). Furin recognition motif underlined.
*Also referred to as hFVIII-BDD.
Abbreviations:
aa, amino acids;
c, canine;
cl, cell-line;
F, factor;
h, human;
NA, not applicable;
p, porcine.
Provided amino acid sequences are SEQ ID NOs: 3-12, from top to bottom.

Herein, novel Factor VIII variants are provided. The instant invention encompasses FVIII variants including FVIIIa variants and FVIII prepeptide variants. For simplicity, the variants are generally described throughout the application in the context of FVIII. However, the invention contemplates and encompasses Factor FVIIIa and FVIII prepeptide molecules having the same amino acid substitutions and/or linkers as described in FVIIL. In a particular embodiment, the FVIII variants of the instant invention are expressed as a single chain molecule or at least almost exclusively as a single chain molecule.

ecules comprising a linker. In a particular embodiment, the linker comprises a sequence set forth in Table 2. As shown herein, the replacement of the B domain of Factor VIII with the sequences set forth in Table 2 yielded Factor VIII variants which exhibit enhanced Factor VIII activity. These FVIII variants were also expressed to higher levels than other BDD FVIII. Moreover, the linkers provided in Table 2 have only one neo-epitope each, whereas each of the linkers in Table 1 have more than one neo-epitope. By reducing or minimizing the number of neo-epitopes in the linker region, the adverse immunogenicity of the FVIII variants are reduced with the linkers in Table 2.

TABLE 2

New B-domain linkers with minimal neo-epitopes Provided amino acid sequences are SEQ ID NOs 13-18, from top to bottom

| Variant | Amino Acids | Neo-epitopes | Sequence (740-) |
|---|---|---|---|
| B1 | 10 | 1 | SFSQNSRHPS |
| B2 | 15 | 1 | SFSQNSRHPSTRQKQ |
| B3 | 20 | 1 | SFSQNSRHPSTRQKQFNATT |
| B4 | 5 | 1 | SFSQN |
| B5 | 8 | 1 | SFSQNSRH |
| B6 | 30 | 1 | SFSQNSRHPSTRQKCIFNATTIPENDIEKTD |

The FVIII variants of the instant invention can be from any mammalian species. In a particular embodiment, the FVIII variant is human. Gene ID: 2157 and GenBank Accession Nos. NM_000132.3 and NP_000123.1 provide examples of the amino acid and nucleotide sequences of wild-type human FVIII (particularly the prepeptide comprising the signal peptide). FIG. 4 provides SEQ ID NO: 1, which is an example of the amino acid sequence of human FVIII. SEQ ID NO: 1 lacks the 19 amino acid signal peptide at its N-terminus (MQIELSTCFFLCLLRFCFS (SEQ ID NO: 2)). Nucleic acid molecules which encode Factor FVIII variants can be readily determined from the provided amino acid sequences as well as the provided GenBank Accession Nos.

In accordance with one aspect of the instant invention, the FVIII variants are B-domain deleted (BDD) FVIII mol- In a particular embodiment, the instant invention encompasses FVIII variants wherein the B-domain (e.g., amino acids 741-1648 of SEQ ID NO: 1) is replaced with an amino acid sequence comprising or consisting of SEQ ID NO: 13, SEQ ID NO: 14, SEQ ID NO: 15, SEQ ID NO: 16, SEQ ID NO: 17, or SEQ ID NO: 18. In a particular embodiment, the B-domain is replaced with an amino acid sequence up to about 50, up to about 45, up to about 40, up to about 35, up to about 30, up to about 25, up to about 20, up to about 15, up to about 10, or up to about 5 amino acids in length. In a particular embodiment, the B-domain (e.g., amino acids 741-1648 of SEQ ID NO: 1) is replaced with an amino acid sequence comprising or consisting of SEQ ID NO: 17 or SEQ ID NO: 18. In a particular embodiment, the B-domain (e.g., amino acids 741-1648 of SEQ ID NO: 1) is replaced with an amino acid sequence comprising or consisting of SEQ ID NO: 18. In a particular embodiment, the B-domain (e.g., amino acids 741-1648 of SEQ ID NO: 1) is replaced with an amino acid sequence having at least 75%, 80%, 85%, 90%, 95%, 97%, 99%, or 100% homology (identity) with SEQ ID NO: 13, SEQ ID NO: 14, SEQ ID NO: 15, SEQ ID NO: 16, SEQ ID NO: 17, or SEQ ID NO: 18, particularly at least 90%, 95%, 97%, 99%, or 100% homology (identity). In a particular embodiment, the B-domain (e.g., amino acids 741-1648 of SEQ ID NO: 1) is replaced with an amino acid sequence having at least 75%, 80%, 85%, 90%, 95%, 97%, 99%, or 100% homology (identity) with SEQ ID NO: 18, particularly at least 90%, 95%, 97%, 99%, or 100% homology (identity).

In accordance with another aspect of the instant invention, the Factor VIII variants comprise at least one mutation at position 560, 561, 712, 713, and/or 659. As seen herein, these FVIII variants possess higher specific activity than wild type FVIII. In certain embodiments, the Factor VIII variants comprise a mutation at position 659. In a particular embodiment, the Lys (K) at position 659 is not substituted with a Pro (P), Gly (G), Met (M), or Leu (L). In a particular embodiment, the Lys at position 659 is substituted with Trp (W), Arg (R), Ala (A), His (H), Tyr (Y), Asp (D), Thr (T), Ser (S), Val (V), Phe (F), Gln (Q), or Cys (C). In a particular embodiment, the Lys at position 659 is substituted with Asp (D), Thr (T), Ser (S), Val (V), Phe (F), Gln (Q), or Cys (C). In a particular embodiment, the Lys at position 659 is substituted with Ser (S), Val (V), Phe (F), Gln (Q), or Cys (C). In a particular embodiment, the Lys at position 659 is substituted with Ser (S), Gln (Q), or Cys (C). In a particular embodiment, the Lys at position 659 is substituted with Gln (Q) or Cys (C).

In certain embodiments, the Factor VIII variants comprise a mutation at position 560. In a particular embodiment, the Asp (D) at position 560 is substituted with Ala (A), Val (V), Ile (I), Leu (L), His (H), Arg (R), or Lys (K). In a particular embodiment, the Asp (D) at position 560 is substituted with Ala (A), Val (V), Ile (I), or Leu (L). In a particular embodiment, the Asp (D) at position 560 is substituted with His (H), Arg (R), or Lys (K). In a particular embodiment, the Asp (D) at position 560 is substituted with Ile (I) or His (H).

In certain embodiments, the Factor VIII variants comprise a mutation at position 561. In a particular embodiment, the Gln (Q) at position 561 is not substituted with Leu (L), Arg (R), or Asn (N). In a particular embodiment, the Gln (Q) at position 561 is substituted with Asp (D) or Glu (E). In a particular embodiment, the Gln (Q) at position 561 is substituted with Asp (D).

In certain embodiments, the Factor VIII variants comprise a mutation at position 712. In a particular embodiment, the Asp (D) at position 712 is substituted with an amino acid other than Glu (E). In a particular embodiment, the Asp (D) at position 712 is substituted with Ala (A), Val (V), Ile (I), or Leu (L). In a particular embodiment, the Asp (D) at position 712 is substituted with Ile (I) or Leu (L). In a particular embodiment, the Asp (D) at position 712 is substituted with Leu (L).

In certain embodiments, the Factor VIII variants comprise a mutation at position 713. In a particular embodiment, the Lys (K) at position 713 is substituted with Ala (A), Arg (R), Met (M), Tyr (Y), Asp (D), Glu (E), Cys (C), or Gly (G). In a particular embodiment, the Lys (K) at position 713 is substituted with Arg (R), Met (M), Tyr (Y), Asp (D), Cys (C), or Gly (G). In a particular embodiment, the Lys (K) at position 713 is substituted with Asp (D) or Glu (E). In a particular embodiment, the Lys (K) at position 713 is substituted with Cys (C). In a particular embodiment, the Lys (K) at position 713 is substituted with Ala (A) or Gly (G). In a particular embodiment, the Lys (K) at position 713 is substituted with Gly (G).

The FVIII variants of the instant invention may comprise at least one mutation at position 560, 561, 712, 713, and/or 659 as described herein and/or comprise a linker in place of the B-domain as described herein. In other words, the instant invention encompasses FVIII variants with only a mutation at position 560, 561, 712, 713, and/or 659 (e.g., the FVIII comprises a full B domain), FVIII variants with only a linker in place of the B-domain (e.g., the amino acids at positions 560, 561, 712, 713, and 659 are wild-type), and FVIII variants comprising a mutation at position 560, 561, 712, 713, and/or 659 and a linker in place of the B-domain.

In a particular embodiment, the FVIII variant comprises a mutation at position 560, 561, 712, 713, and/or 659 and a linker in place of the B-domain. In a particular embodiment, the FVIII variant comprises a mutation at position 560, 561, 712, 713, and/or 659 and a linker in place of the B-domain having an amino acid sequence having at least 75%, 80%, 85%, 90%, 95%, 97%, 99%, or 100% homology (identity) with SEQ ID NO: 13, SEQ ID NO: 14, SEQ ID NO: 15, SEQ ID NO: 16, SEQ ID NO: 17, or SEQ ID NO: 18, particularly at least 90%, 95%, 97%, 99%, or 100% homology. In a particular embodiment, the FVIII variant comprises a mutation at position 560, 561, 712, 713, and/or 659 and a linker in place of the B-domain having an amino acid sequence having at least 75%, 80%, 85%, 90%, 95%, 97%, 99%, or 100% homology (identity) with SEQ ID NO: 18, particularly at least 90%, 95%, 97%, 99%, or 100% homology (identity). In certain embodiments, the Factor VIII variants comprise a mutation at position 659. In a particular embodiment, the Lys (K) at position 659 is not substituted with a Pro (P), Gly (G), Met (M), or Leu (L). In a particular embodiment, the Lys at position 659 is substituted with Trp (W), Arg (R), Ala (A), His (H), Tyr (Y), Asp (D), Thr (T), Ser (S), Val (V), Phe (F), Gln (Q), or Cys (C). In a particular embodiment, the Lys at position 659 is substituted with Asp (D), Thr (T), Ser (S), Val (V), Phe (F), Gln (Q), or Cys (C). In a particular embodiment, the Lys at position 659 is substituted with Ser (S), Val (V), Phe (F), Gln (Q), or Cys (C). In a particular embodiment, the Lys at position 659 is substituted with Ser (S), Gln (Q), or Cys (C). In a particular embodiment, the Lys at position 659 is substituted with Gln (Q) or Cys (C). In certain embodiments, the Factor VIII variants comprise a mutation at position 560. In a particular embodiment, the Asp (D) at position 560 is substituted with Ala (A), Val (V), Ile (I), Leu (L), His (H), Arg (R), or Lys (K). In a particular embodiment, the Asp (D) at position 560 is substituted with Ala (A), Val (V), Ile (I), or Leu (L). In a particular embodiment, the Asp (D) at position 560 is substituted with His (H), Arg (R), or Lys (K). In a particular embodiment, the Asp (D) at position 560 is substituted with Ile (I) or His (H). In certain embodiments, the Factor VIII variants comprise a mutation at position 561. In a particular embodiment, the Gln (Q) at position 561 is not substituted with Leu (L), Arg (R), or Asn (N). In a particular embodiment, the Gln (Q) at position 561 is substituted with Asp (D) or Glu (E). In a particular embodiment, the Gln (Q) at position 561 is substituted with Asp (D). In certain embodiments, the Factor VIII variants comprise a mutation at position 712. In a particular embodiment, the Asp (D) at position 712 is substituted with an amino acid other than Glu (E). In a particular embodiment, the Asp (D) at position 712 is substituted with Ala (A), Val (V), Ile (I), or Leu (L). In a particular embodiment, the Asp (D) at position 712 is substituted with Ile (I) or Leu (L). In a particular embodiment, the Asp (D) at position 712 is substituted with Leu (L). In certain embodiments, the Factor VIII variants comprise a mutation at position 713. In a particular embodiment, the Lys (K) at position 713 is substituted with Ala (A), Arg (R), Met (M), Tyr (Y), Asp (D), Glu (E), Cys (C), or Gly (G). In a particular embodiment, the Lys (K) at position 713 is substituted with Arg (R), Met (M), Tyr (Y), Asp (D), Cys (C), or Gly (G). In a particular embodiment, the Lys (K) at position 713 is substituted with Asp (D) or Glu (E). In a particular embodiment, the Lys (K) at position 713 is substituted with Cys (C). In a particular embodiment, the Lys (K) at position 713 is substituted with Ala (A) or Gly (G). In a particular embodiment, the Lys (K) at position 713 is substituted with Gly (G).

As stated hereinabove, the FVIII variant of the instant invention may be human. In a particular embodiment, the FVIII variant of the instant invention has at least 75%, 80%, 85%, 90%, 95%, 97%, 99%, or 100% homology (identity) with SEQ ID NO: 1 (or an activated FVIII fragment thereof), particularly at least 90%, 95%, 97%, 99%, or 100% homology (identity). In a particular embodiment, the FVIII variant comprises an amino acid sequence having at least 75%, 80%, 85%, 90%, 95%, 97%, 99%, or 100% homology (identity), particularly at least 90%, 95%, 97%, 99%, or 100% homology (identity), with amino acids 1-740 of SEQ ID NO: 1 (or an activated FVIII fragment thereof) and an amino acid sequence having at least 75%, 80%, 85%, 90%, 95%, 97%, 99%, or 100% homology (identity), particularly at least 90%, 95%, 97%, 99%, or 100% homology (identity) with amino acids 1649-2332 of SEQ ID NO: 1 (or an activated FVIII fragment thereof). The homology (identity) percentages above exclude the substitutions at position 560, 561, 712, 713, and/or 659.

The FVIII variants of the instant invention may also be post-translationally modified. The FVIII variants may be post-translationally modified in a cell (particularly a human cell) or in vitro.

In a particular embodiment, the FVIII variants of the instant invention have increased expression compared to wild-type FVIII or hFVIII-SQ. In a particular embodiment, the FVIII variants of the invention have increased FVIII activity or increased specific activity compared to wild-type FVIII.

Nucleic acid molecules encoding the above FVIII variants are also encompassed by the instant invention. Nucleic acid molecules encoding the variants may be prepared by any method known in the art. The nucleic acid molecules may be maintained in any convenient vector, particularly an expression vector.

Compositions comprising at least one FVIII variant and at least one carrier are also encompassed by the instant invention. In a particular embodiment, the FVIII is isolated and/or substantially pure within the composition. Compositions comprising at least one FVIII variant nucleic acid molecule and at least one carrier are also encompassed by the instant invention. Except insofar as any conventional carrier is incompatible with the variant to be administered, its use in the pharmaceutical composition is contemplated. In a particular embodiment, the carrier is a pharmaceutically acceptable carrier for intravenous administration.

Definitions

Various terms relating to the biological molecules of the present invention are used hereinabove and also throughout the specification and claims.

The phrase "hemostasis related disorder" refers to bleeding disorders such as, without limitation, hemophilia A, hemophilia B, hemophilia A and B patients, hemophilia with inhibitory antibodies, deficiencies in at least one coagulation factor (e.g., Factors VII, VIII, IX, X, XI, V, XII, II, and/or von Willebrand factor, particularly Factor VIII), combined FV/FVIII deficiency, vitamin K epoxide reductase C1 deficiency, gamma-carboxylase deficiency, bleeding associated with trauma or injury, thrombosis, thrombocytopenia, stroke, coagulopathy (hypocoagulability), disseminated intravascular coagulation (DIC), over-anticoagulation associated with heparin, low molecular weight heparin, pentasaccharide, warfarin, or small molecule antithrombotics (e.g., FXa inhibitors); and platelet disorders such as, Bernard Soulier syndrome, Glanzman thromblastemia, and storage pool deficiency. In a particular embodiment, the term "hemostasis related disorder" refers to bleeding disorders characterized by excessive and/or uncontrolled bleeding (e.g., a disorder which can be treated with a procoagulant). In a particular embodiment, the hemostasis related disorder is hemophilia. In a particular embodiment, the hemostasis related disorder is hemophilia A.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote. With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

With respect to protein, the term "isolated protein" is sometimes used herein. This term may refer to a protein produced by expression of an isolated nucleic acid molecule of the invention. Alternatively, this term may refer to a protein which has been sufficiently separated from other proteins with which it would naturally be associated (e.g., so as to exist in "substantially pure" form). "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "vector" refers to a carrier nucleic acid molecule (e.g., RNA or DNA) into which a nucleic acid sequence can be inserted for introduction into a host cell where it will be replicated. An "expression vector" is a specialized vector that contains a gene or nucleic acid sequence with the necessary regulatory regions (e.g., promoter) needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.), particularly at least 75% by weight, or at least 90-99% or more by weight of the compound of interest. Purity may be measured by methods appropriate for the compound of interest (e.g. chromatographic methods, agarose or polyacrylamide gel electrophoresis, HPLC analysis, and the like).

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

Preparation of Variant Encoding Nucleic Acid Molecules and Polypeptides

Nucleic acid molecules encoding the variants of the invention may be prepared by using recombinant DNA technology methods. The availability of nucleotide sequence information enables preparation of isolated nucleic acid molecules of the invention by a variety of means. For example, nucleic acid sequences encoding a variant may be isolated from appropriate biological sources using standard protocols well known in the art.

Nucleic acids of the present invention may be maintained as RNA or DNA in any convenient cloning vector. In a particular embodiment, clones are maintained in a plasmid cloning/expression vector (e.g., pBluescript (Stratagene, La Jolla, CA)), which is propagated in a suitable E. coli host cell. Alternatively, the nucleic acids may be maintained in a vector suitable for expression in mammalian cells. In cases where post-translational modification affects variant function, it is preferable to express the molecule in mammalian cells, particularly human cells.

FVIII variant encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting variant expression.

The FVIII variants of the present invention may be prepared in a variety of ways, according to known methods.

The protein may be purified from appropriate sources (e.g., transformed bacterial or animal (e.g., mammalian or human) cultured cells or tissues which express FVIII variants), for example, by immunoaffinity purification. The availability of nucleic acid molecules encoding the variants enables production of the variants using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega or Life Technologies.

Alternatively, larger quantities of variant may be produced by expression in a suitable prokaryotic or eukaryotic expression system. For example, part or all of a DNA molecule encoding the FVIII variant may be inserted into a plasmid vector adapted for expression in a bacterial cell, such as E. coli, or a mammalian cell (particularly a human cell) such as CHO or HeLa cells. Alternatively, tagged fusion proteins comprising the variant can be generated. Such variant-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as E. coli or a eukaryotic cell, such as, but not limited to, yeast and mammalian cells, particularly human cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

FVIII variant proteins, produced by gene expression in a recombinant prokaryotic or eukaryotic system (particularly human) may be purified according to methods known in the art. In a particular embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise, without limitation, the FLAG epitope, GST or the hemagglutinin epitope. Such methods are commonly used by skilled practitioners.

FVIII variant proteins, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems, such as in reticulocyte lysates.

Uses of FVIII Variant Proteins and Variant-Encoding Nucleic Acids

FVIII variant proteins and nucleic acids of the instant invention may be used, for example, as therapeutic and/or prophylactic agents which modulate the blood coagulation cascade. It is demonstrated herein that the FVIII variants possess superior properties and can provide effective hemostasis.

In a particular embodiment of the present invention, FVIII variants may be administered to a patient via infusion in a biologically compatible carrier, e.g., via intravenous injection. The FVIII variants of the invention may optionally be encapsulated into liposomes or mixed with other phospholipids or micelles to increase stability of the molecule. FVIII variants may be administered alone or in combination with other agents known to modulate hemostasis (e.g., vFW, Factor IX, Factor IXa, etc.). An appropriate composition in which to deliver the FVIII variant may be determined by a medical practitioner upon consideration of a variety of physiological variables, including, but not limited to, the patient's condition and hemodynamic state. A variety of compositions well suited for different applications and routes of administration are well known in the art and are described hereinbelow.

The preparation containing the FVIII variants may contain a physiologically acceptable matrix and is formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing the FVIII variant can be stored in the form of a finished solution or in lyophilized or deep-frozen form. In a particular embodiment, the preparation is stored in lyophilized form and is dissolved into a visually clear solution using an appropriate reconstitution solution. Alternatively, the preparation according to the present invention can also be made available as a liquid preparation or as a liquid that is deep-frozen. The preparation according to the present invention may be especially stable, i.e., it can be allowed to stand in dissolved form for a prolonged time prior to application.

The preparation according to the present invention can be made available as a pharmaceutical preparation with the FVIII variant in the form of a one-component preparation or in combination with other factors in the form of a multi-component preparation.

Prior to processing the purified protein into a pharmaceutical preparation, the purified protein may be subjected to the conventional quality controls and fashioned into a therapeutic form of presentation. In particular, during the recombinant manufacture, the purified preparation may be tested for the absence of cellular nucleic acids as well as nucleic acids that are derived from the expression vector.

Another feature of this invention relates to making available a preparation which contains a FVIII variant with a high stability and structural integrity and which, in particular, is free from inactive FVIII intermediates and/or proteolytic degradation products and by formulating it into an appropriate preparation.

The pharmaceutical preparation may contain, as an example, dosages of between about 1-1000 µg/kg, about 10-500 µg/kg, about 10-250 µg/kg, or about 10-100 µg/kg. In a particular embodiment, the pharmaceutical protein preparation may comprise a dosage of between 30-100 IU/kg (e.g., as a single daily injection or up to 3 times or more/day). Patients may be treated immediately upon presentation at the clinic with a bleed or prior to the delivery of cut/wound causing a bleed. Alternatively, patients may receive a bolus infusion every one to three, eight, or twelve hours or, if sufficient improvement is observed, a once daily infusion of the FVIII variant described herein.

FVIII variant-encoding nucleic acids may be used for a variety of purposes in accordance with the present invention. In a particular embodiment of the invention, a nucleic acid delivery vehicle (e.g., an expression vector such as a viral vector) for modulating blood coagulation is provided wherein the expression vector comprises a nucleic acid sequence coding for a FVIII variant as described herein. Administration of the FVIII variant-encoding expression vectors to a patient results in the expression of the FVIII variant which serves to alter the coagulation cascade. In accordance with the present invention, a FVIII variant encoding nucleic acid sequence may encode a variant polypeptide as described herein whose expression increases hemostasis. In a particular embodiment, the nucleic acid sequence encodes a human FVIII variant.

Expression vectors comprising FVIII variant nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible composition.

In a particular embodiment of the invention, the expression vector comprising nucleic acid sequences encoding the FVIII variant is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-1 to AAV-12, particularly AAV-2, AAV-5, AAV-7, and AAV-8) and hybrid AAV vectors, lentivirus vectors and pseudo-typed lentivirus vectors (e.g., Ebola virus, vesicular stomatitis virus (VSV), and feline immunodeficiency virus (FIV)), herpes simplex virus vectors, vaccinia virus vectors, and retroviral vectors. In a particular embodiment, the vector is an adeno-associated virus (AAV) vector. In a particular embodiment, the vector is a lentiviral vector.

In a particular embodiment of the present invention, methods are provided for the administration of a viral vector comprising nucleic acid sequences encoding a FVIII variant. Adenoviral vectors of utility in the methods of the present invention preferably include at least the essential parts of adenoviral vector DNA. As described herein, expression of a FVIII variant following administration of such an adenoviral vector serves to modulate hemostasis, particularly to enhance the procoagulation activity of the protease.

Recombinant adenoviral vectors have found broad utility for a variety of gene therapy applications. Their utility for such applications is due largely to the high efficiency of in vivo gene transfer achieved in a variety of organ contexts.

Adenoviral particles may be used to advantage as vehicles for adequate gene delivery. Such virions possess a number of desirable features for such applications, including: structural features related to being a double stranded DNA nonenveloped virus and biological features such as a tropism for the human respiratory system and gastrointestinal tract. Moreover, adenoviruses are known to infect a wide variety of cell types in vivo and in vitro by receptor-mediated endocytosis. Attesting to the overall safety of adenoviral vectors, infection with adenovirus leads to a minimal disease state in humans comprising mild flu-like symptoms.

Due to their large size (~36 kilobases), adenoviral genomes are well suited for use as gene therapy vehicles because they can accommodate the insertion of foreign DNA following the removal of adenoviral genes essential for replication and nonessential regions. Such substitutions render the viral vector impaired with regard to replicative functions and infectivity. Of note, adenoviruses have been used as vectors for gene therapy and for expression of heterologous genes.

It is desirable to introduce a vector that can provide, for example, multiple copies of a desired gene and hence greater amounts of the product of that gene. Improved adenoviral vectors and methods for producing these vectors have been described in detail in a number of references, patents, and patent applications, including: Wright (Hum Gen Ther. (2009) 20:698-706); Mitani and Kubo (Curr Gene Ther. (2002) 2(2):135-44); Olmsted-Davis et al. (Hum Gene Ther. (2002) 13(11):1337-47); Reynolds et al. (Nat Biotechnol. (2001) 19(9):838-42); U.S. Pat. No. 5,998,205 (wherein tumor-specific replicating vectors comprising multiple DNA copies are provided); 6,228,646 (wherein helper-free, totally defective adenovirus vectors are described); 6,093,699 (wherein vectors and methods for gene therapy are provided); 6,100,242 (wherein a transgene-inserted replication defective adenovirus vector was used effectively in in vivo gene therapy of peripheral vascular disease and heart disease); and International Patent Application Nos. WO 94/17810 and WO 94/23744.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of the variant or functional fragments thereof. For example, an E1 deleted type 5 adenoviral vector comprising nucleic acid sequences encoding variant under the control of a cytomegalovirus (CMV) promoter may be used to advantage in the methods of the present invention. Hematopoietic or liver specific promoters may also be used.

AAV for recombinant gene expression have been produced in the human embryonic kidney cell line 293 (Wright, Hum Gene Ther (2009) 20:698-706; Graham et al. (1977) J. Gen. Virol. 36:59-72). Briefly, AAV vectors are typically engineered from wild-type AAV, a single-stranded DNA virus that is non-pathogenic. The parent virus is non-pathogenic, the vectors have a broad host range, and they can infect both dividing and non-dividing cells. The vector is typically engineered from the virus by deleting the rep and cap genes and replacing these with the transgene of interest under the control of a specific promoter. For recombinant AAV preparation, the upper size limit of the sequence that can be inserted between the two ITRs is about 4.7 kb. Plasmids expressing a FVIII variant under the control of the CMV promoter/enhancer and a second plasmid supplying adenovirus helper functions along with a third plasmid containing the AAV-2 rep and cap genes may be used to produce AAV-2 vectors, while a plasmid containing either AAV-1, AAV-6, or AAV-8 cap genes and AAV-2 rep gene and ITR's may be used to produce the respective alternate serotype vectors (e.g., Gao et al. (2002) Proc. Natl. Acad. Sci. USA 99:11854-11859; Xiao et al., (1999) J. Virol. 73:3994-4003; Arruda et al., (2004) Blood 103:85-92). AAV vectors may be purified by repeated CsCl density gradient centrifugation and the titer of purified vectors determined by quantitative dot-blot hybridization. In a particular embodiment, vectors may be prepared by the Vector Core at The Children's Hospital of Philadelphia.

Also included in the present invention is a method for modulating hemostasis comprising providing cells of an individual with a nucleic acid delivery vehicle encoding a FVIII variant and allowing the cells to grow under conditions wherein the FVIII variant is expressed.

From the foregoing discussion, it can be seen that FVIII variants and FVIII variant expressing nucleic acid vectors may be used in the treatment of disorders associated with aberrant blood coagulation.

The expression vectors of the present invention may be incorporated into pharmaceutical compositions that may be delivered to a subject, so as to allow production of a biologically active protein (e.g., a FVIII variant) or by inducing expression of the FVIII variant in vivo by gene- and or cell-based therapies or by ex vivo modification/transduction of the patient's or donor's cells. In a particular embodiment of the present invention, pharmaceutical compositions comprising sufficient genetic material to enable a recipient to produce a therapeutically effective amount of a FVIII variant can influence hemostasis in the subject. Alternatively, as discussed above, an effective amount of the FVIII variant may be directly infused into a patient in need thereof. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents (e.g., co-factors) which influence hemostasis.

In particular embodiments, the pharmaceutical compositions also contain a pharmaceutically acceptable excipient/carrier. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they may be placed in an appropriate container and labeled for treatment. For administration of FVIII variants or FVIII variant encoding vectors, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided in the present invention. Therapeutic doses will depend on, among other factors, the age and general condition of the subject, the severity of the aberrant blood coagulation phenotype, and the strength of the control sequences regulating the expression levels of the variant polypeptide. Thus, a therapeutically effective amount in humans will fall in a relatively broad range that may be determined by a medical practitioner based on the response of an individual patient to vector-based variant treatment.

The FVIII variants, alone or in combination with other agents may be directly infused into a patient in an appropriate biological carrier as described hereinabove. Expression vectors of the present invention comprising nucleic acid sequences encoding variant or functional fragments thereof, may be administered to a patient by a variety of means (see below) to achieve and maintain a prophylactically and/or therapeutically effective level of the variant polypeptide. One of skill in the art could readily determine specific protocols for using the variant encoding expression vectors of the present invention for the therapeutic treatment of a particular patient. Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94/23744, which are incorporated herein by reference in their entirety.

FVIII variant encoding adenoviral vectors of the present invention may be administered to a patient by any means known. Direct delivery of the pharmaceutical compositions in vivo may generally be accomplished via injection using a conventional syringe, although other delivery methods such as convection-enhanced delivery are envisioned (See e.g., U.S. Pat. No. 5,720,720). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications. A clinician specializing in the treatment of patients with blood coagulation disorders may determine the optimal route for administration of the adenoviral vectors comprising variant nucleic acid sequences based on a number of criteria, including, but not limited to: the condition of the patient and the purpose of the treatment (e.g., enhanced or reduced blood coagulation).

The present invention also encompasses AAV vectors comprising a nucleic acid sequence encoding a FVIII variant. Also provided are lentiviruses or pseudo-typed lentivirus vectors comprising a nucleic acid sequence encoding a FVIII variant. Also encompassed are naked plasmid or expression vectors comprising a nucleic acid sequence encoding a FVIII variant.

The following examples are provided to illustrate various embodiments of the present invention. The examples are illustrative and are not intended to limit the invention in any way.

Example 1

Figure 2:
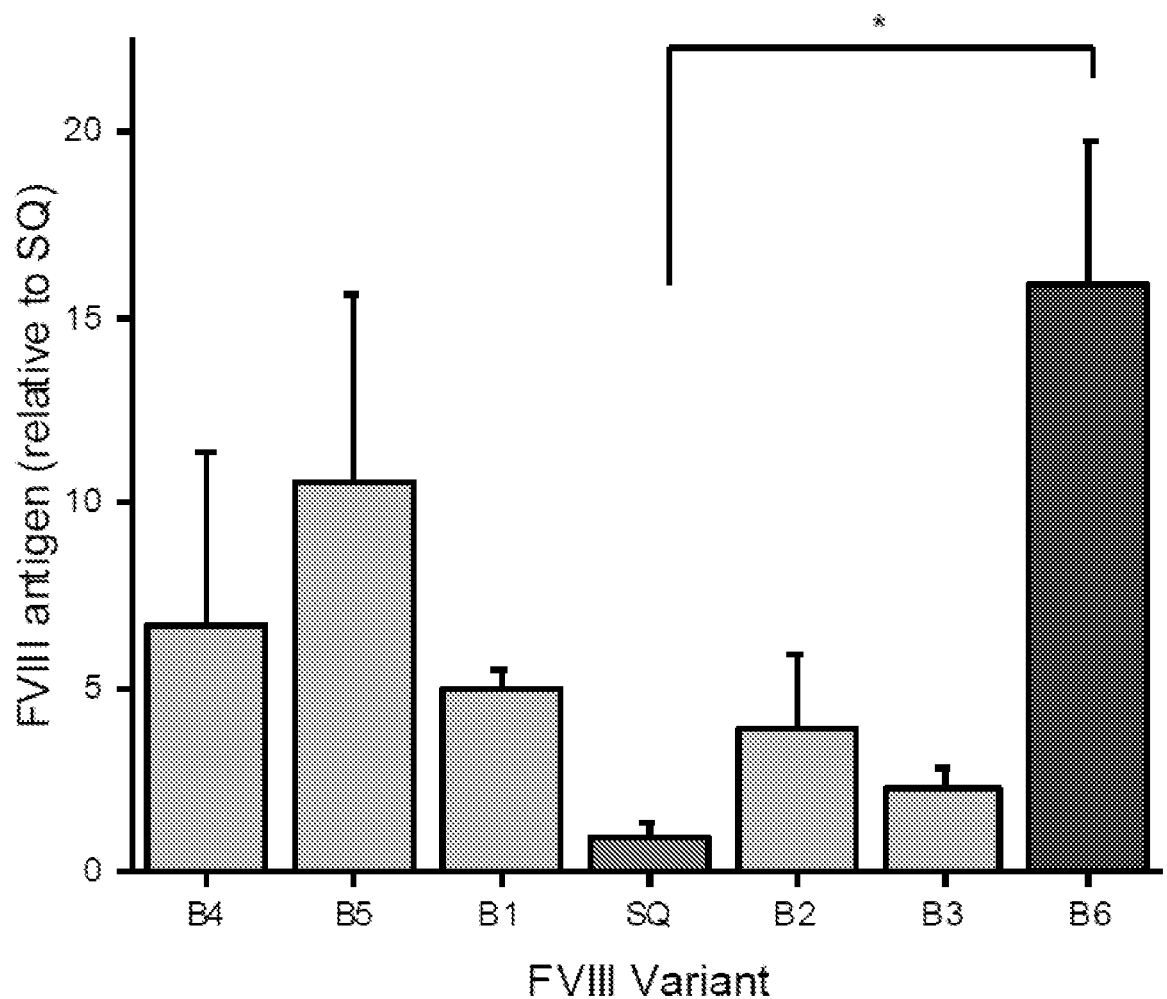
FIG. 2 provides a graph of the expression of various human FVIII B domain variants in hemophilia A mice.

Non-viral vector (naked DNA, 5 μg/mouse) expressing various human FVIII B domain variants and FVIII-SQ under the control of a liver-specific promoter was injected by tail vein route under hydrodynamic condition (5 mice/variant). The Variant B domains tested were: B1: SFSQNSRHPS (SEQ ID NO: 13); B2: SFSQNSRHPSTRQKQ (SEQ ID NO: 14); B3: SFSQNSRHPSTRQKQFNATT (SEQ ID NO: 15); B4: SFSQN (SEQ ID NO: 16); B5: SFSQNSRH (SEQ ID NO: 17); and B6: SFSQNSRHPSTRQKQFNATTI-PENDIEKTD (SEQ ID NO: 18). After 24 hours, blood was collected and FVIII antigen levels were measured by ELISA using the Affinity Biologicals Matched Pair Antibody Set Product #F8C-EIA. As seen in FIG. 2, all of the human FVIII B domain variants of the instant invention were expressed in hemophilia A mice to higher levels than FVIII-SQ.

Example 2

Figure 3:
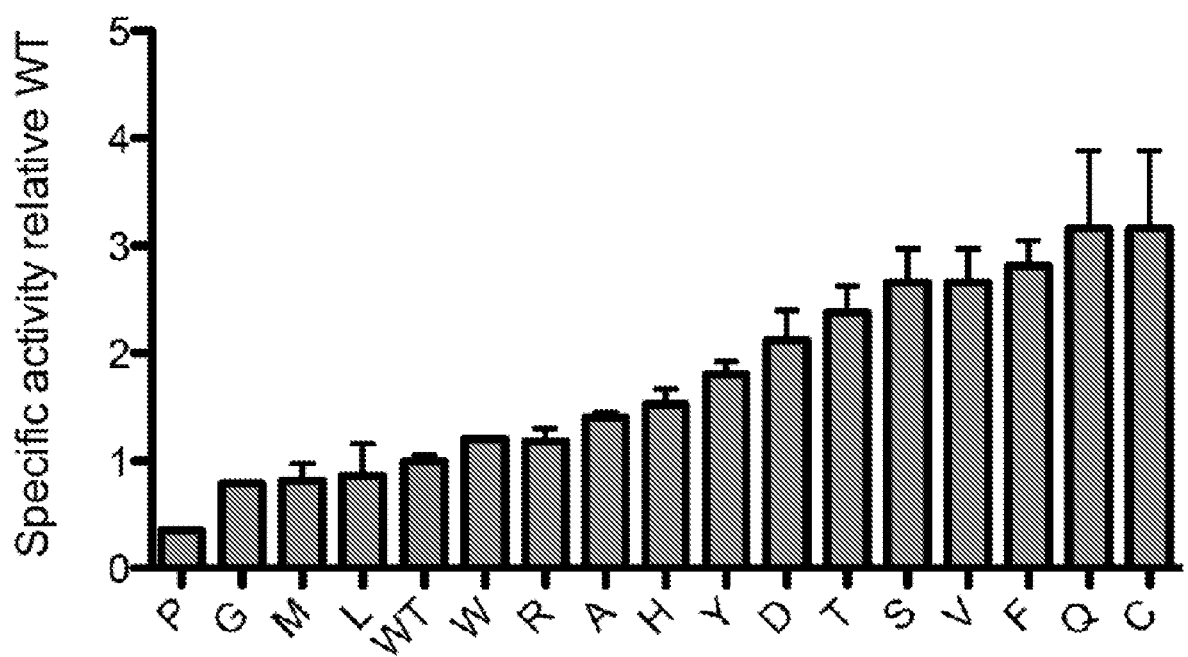
FIG. 3 provides a graph of FVIII specific activity of variants with amino acid substitutions at position 659.

Wild-type FVIII (659K) and amino acid substitution variants thereof were transiently expressed in BHK cells. The specific activity of the expressed FVIII were determined by one-stage aPTT assay in conditioned expression media. As seen in FIG. 3, most of the FVIII variants showed increased specific activity compared to wild-type FVIII.

Example 3

Figure 5:
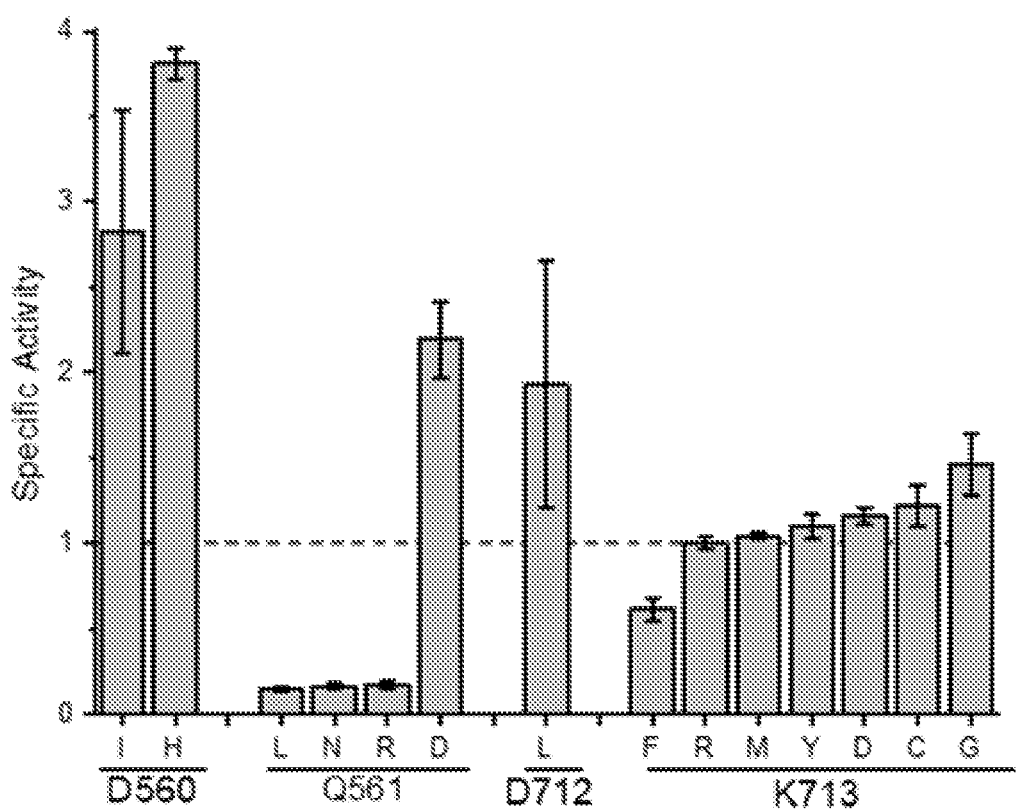
FIG. 5 provides a graph of FVIII specific activity of variants with amino acid substitutions at positions 560, 561, 712, and 713.

In addition to the FVIII variants with amino acid substitutions at position 659, FVIII variants with substitutions at 560, 561, 712, and 713 were also tested by transient expression in BHK cells. The specific activity of the expressed FVIII were determined by one-stage aPTT assay in conditioned expression media. As seen in FIG. 5, variants with amino acid substitutions at each position demonstrated enhanced specific activity relative to wild-type FVIII. Combinations of these substitutions, as well as the ones provided in Example 2, can produce FVIII variants with even higher specific activity.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A Factor VIII (FVIII) variant, wherein said FVIII variant comprises SEQ ID NO: 1, except (i) wherein the Lys at position 659 is substituted with another amino acid, (ii) wherein the amino acids at positions 560, 561, 712, and 713 may be optionally substituted with another amino acid, and (wherein the B-domain, consisting of amino acids 741-1648 of SEQ ID NO: 1, is replaced with an amino acid sequence which shares at least 90% sequence identity with SEQ ID NO: 13, SEQ ID NO: 14, SEQ ID NO: 15, SEQ ID NO: 16, SEQ ID NO: 17, or SEQ ID No: 18.

2. The FVIII variant of claim 1, wherein the B-domain is replaced with an amino acid sequence consisting of SEQ ID NO: 13, SEQ ID NO: 14, SEQ ID NO: 15, SEQ ID NO: 16, SEQ ID NO: 17, or SEQ ID NO: 18.

3. The FVIII variant of claim 1, wherein the B-domain is replaced with an amino acid sequence consisting of SEQ ID NO: 18.

4. The FVIII variant of claim 1, further comprising a substitution mutation of the Asp at position 560, the Gln at position 561, the Asp at position 712, and/or the Lys at position 713.

5. A Factor VIII (FVIII) variant, wherein said FVIII variant comprises amino acids 1-740 and 1649-2332 of SEQ ID NO: 1, except (i) wherein the Lys at position 659 is substituted with another amino acid, and (ii) wherein the amino acids at positions 560, 561, 712, and 713 may be optionally substituted with another amino acid.

6. The FVIII variant of claim 5, wherein the Lys at position 659 is substituted with Trp, Arg, Ala, His, Tyr, Asp, Thr, Ser, Val, Phe, Gln, or Cys.

7. The FVIII variant of claim 5, further comprising a substitution mutation of the Asp at position 560.

8. The FVIII variant of claim 5, further comprising a substitution mutation of the Gln at position 561.

9. The FVIII variant of claim 5, further comprising a substitution mutation of the Asp at position 712.

10. The FVIII variant of claim 5, further comprising a substitution mutation of the Lys at position 713.

11. A composition comprising at least one FVIII variant of claim 1 and at least one pharmaceutically acceptable carrier.

12. A method for treatment of a hemostasis related disorder in a patient in need thereof comprising administration of a therapeutically effective amount of the FVIII variant of claim 1 in a pharmaceutically acceptable carrier.

13. The method of claim 12, wherein said hemostasis related disorder is hemophilia A.

14. An isolated nucleic acid molecule encoding the FVIII variant of claim 1, optionally wherein said FVIII variant comprises a signal peptide.

15. An expression vector comprising the nucleic acid molecule of claim 14 operably linked to a regulatory sequence, optionally wherein the vector is selected from the group consisting of an adenoviral vector, an adenovirus-associated vector, a retroviral vector, a plasmid, and a lentiviral vector.

16. A host cell comprising the vector of claim 15, optionally wherein said host cells are human cells.

17. A method for treatment of a hemostasis related disorder in a patient in need thereof comprising administration of a therapeutically effective amount of the vector of claim 15 in a pharmaceutically acceptable carrier.

18. The FVIII variant of claim 5, wherein the Lys at position 659 is substituted with Cys.

19. A composition comprising at least one FVIII variant of claim 5 and at least one pharmaceutically acceptable carrier.

20. The FVIII variant of claim 1, wherein the Lys at position 659 is substituted with Trp, Arg, Ala, His, Tyr, Asp, Thr, Ser, Val, Phe, Gln, or Cys.

21. The FVIII variant of claim 1, wherein the Lys at position 659 is substituted with Val, Phe, Ser, Gln, or Cys.

22. The FVIII variant of claim 1, wherein the Lys at position 659 is substituted with Val.

23. The FVIII variant of claim 5, wherein the Lys at position 659 is substituted with Val, Phe, Ser, Gln, or Cys.

24. The FVIII variant of claim 5, wherein the Lys at position 659 is substituted with Val.

25. The FVIII variant of claim 1, wherein the B-domain is replaced with an amino acid sequence consisting of SEQ ID NO: 13.

26. The FVIII variant of claim 25, wherein the Lys at position 659 is substituted with Val.

27. A heterotrimeric FVIIIa variant comprising amino acids 1-372, 373-740, and 1690-2332 of SEQ ID NO: 1, except (i) wherein the Lys at position 659 is substituted with another amino acid, and (ii) wherein the amino acids at positions 560, 561, 712, and 713 may be optionally substituted with another amino acid.

* * * * *